United States Patent [19] [11] 4,314,989
Rosen [45] Feb. 9, 1982

[54] METHIONINE SULFOXIDE AMFLIORATION OF ACETAMINOPHEN TOXICITY

[76] Inventor: Gerald M. Rosen, 403 Knob Ct., Chapel Hill, N.C. 27514

[21] Appl. No.: 147,451

[22] Filed: May 7, 1980

[51] Int. Cl.³ ............... A61K 31/195; A61K 31/165
[52] U.S. Cl. .................................. 424/10; 424/319; 424/324
[58] Field of Search ................. 424/319, 324, 10

[56] References Cited
PUBLICATIONS

Crome et al.–Chem. Abst. vol. 86 (1977), p. 37691c.
Prescott et al.–Chem. Abst. vol. 85, (1976) p. 154,118m.

*Primary Examiner*—Sam Rosen
*Attorney, Agent, or Firm*—Millen & White

[57] ABSTRACT

The toxicity in humans of ingested acetaminophen is ameliorated by methionine sulfoxide.

10 Claims, No Drawings

METHIONINE SULFOXIDE AMELIORATION OF ACETAMINOPHEN TOXICITY

BACKGROUND OF THE INVENTION

This invention relates to novel methods and compositions of matter for the amelioration of acetaminophen toxicity in humans.

It has recently been shown that ingestion of therapeutically recommended doses of acetaminophen (paracetamol) in humans for extended periods of time can cause massive hepatic necrosis. A. J. Ware, et al. *Ann. Int. Med.* 88:267-268 (1978); D. M. Rosenberg and F. A. Neelon, *Ann. Int. Med.* 88:129 (1978); J. D. Baker, Jr., *Ann. Int. Med.* 87:299-301 (1977); G. K. Johnson and K. G. Tolman, *Ann. Int. Med.* 87:302-303 (1977); D. M. Rosenberg et al. *South Med. J.*, 70:600-601 (1977); and H. L. Bonkowsky et al. *Lancet* 2:1016-1018 (1978). Recent studies by Nebert with inbred mice have suggested that acetaminophen can cause cataracts in humans (Science 200:539-541, 1978). Finally, conditions which induce the liver enzymes responsible for the activation of acetaminophen such as alcohol or barbiturates will markedly potentiate the hepatotoxicity of this compound.

The mechanism of acetaminophen toxicity is not fully understood. Editorial, Lancet (1975) 2, 1189; B. E. Walker et al., Clin. Sci. & Molecular Med. (1974) 47, 449-459.

Because such diverse compounds as cysteamine, methionine, cysteine, dimethylmercaptol, selenium and vitamin E have afforded varying degrees of protection in man and experimental animals against the hepatotoxicity of acetaminophen and because these compounds under certain circumstances can act as antioxidants, it has been suggested that other antioxidants would also provide protection. J. Kelleher et al., J. Int. Med. Res. (1976) 4, Supplement (4) 138-144.

Animal studies indicate that antioxidants can under some circumstances provide protection against the hepatotoxic effects of acetaminophen. For example, $\alpha$-tocopherol provides such protection in vitamin E deficient rats. Walker et al., supra; J. Kelleher et al., supra. It has been reported that vitamin C also may provide such protection. Raghuram et al., Toxicology Letters, 2 (1978) 175-178. In an experimental study in man, although vitamin C caused a rapid and pronounced decrease in the excretion rate of acetaminophen sulfate, it did not affect the apparent half-life of drug, as evidenced by its rate of secretion in the urine, as such or as its glucuronide or its sulfate. J. B. Houston and G. Levy, J. Pharm. Sci., 65 (1976) 1218-1221. The authors stated that the specific interaction between acetaminophen and ascorbic acid probably was of little clinical significance under usual conditions, i.e., when acetaminophen is taken in single recommended doses as an analgesic or antipyretic. Other researchers concluded that the protective effects manifested by these vitamins cannot be attributed to their antioxidant activity because whereas vitamin E and propyl gallate reduce hepatotoxicity, diphenyl-p-phenylene-diamine (DDPD), an antioxidant in vitro and one which gives protection against $CCl_4$ hepatotoxicity, enhances acetaminophen hepatotoxicity. J. Kelleher et al., J. Int. Med. Res, supra. These authors speculate that the modification of hepatotoxicity may result from an alteration of the activity of the specific components of the microsomol drug metabolizing enzyme system.

Surprisingly and notwithstanding the published literature reporting that some anti-oxidants may provide protection against the hepatotoxic effects of acetaminophen, I have found that the omnipotent antioxidants BHT (butylated hydroxytoluene) and BHA (butylated hydroxyanisole) profoundly enhance its hepatotoxicity. Because the general population consumes large amounts of these chemicals daily, because of their presence in a wide variety of food products, the likelihood of an increased incidence of hepatoxicity in persons taking repeated dosages of acetaminophen is self-evident.

Dimethyl sulfoxide has been shown to protect mice against the hepatotoxic effects of acetaminophen when administered up to one hour after administration of acute toxic amounts of acetaminophen. C. P. Seigers, J. Pharmac. 1978, 30, 375-377. Its activity was attributed to inhibition of microsomal oxidation of the drug by the hepatic mixed-function oxidase system to chemically reactive alkylating agents. On the other hand, this theory would fail to explain the inability of DMSO to protect mice against $CCl_4$ hepatotoxicity, since this compound is also activated by the mixed function oxidase system. The authors therefore conclude that the antihepatotoxic actions of DMSO remain obscure.

A recent news release quotes a publication in "The Medical Letter" which reports a clinical study showing that acetylcysteine is effective in preventing hepatotoxicity if administered within 16 hours after an overdose of acetaminophen. Washington Post, Dec. 7, 1979, page A9. The authors chose acetylcysteine because of its chemical similarity to glutathionine, the substance which the body employs to detoxify the drug.

It is apparent from the foregoing that an effective method of protecting humans against acute acetaminophen hepatotoxicity has yet to be established. Moreover, there is no evidence to date that protection in humans against the chronic toxicity of acetaminophen at therapeutic multiple dosages is possible.

I have found that the anti-oxidant activity of vitamins C and E is not required to avoid the toxic effects of acetaminophen. Moreover, the drug-transport or the chemical similarity to glutathione also is not required. I have found that another class of compounds is effective not only to ameliorate the acute hepatotoxic effects of an overdose of acetaminophen but also to ameliorate the subacute chronic toxic effects of repeated dosages of therapeutic amounts of the drug.

It is an object of this invention to provide a novel method for ameliorating the toxic effects of acetaminophen in humans. It is another object to provide a method for the protection of humans against the acute hepatotoxic effects of an overdose of acetaminophen. It is a further object to provide a method for the protection of humans against the chronic toxic effects of multiple therapeutic doses of acetaminophen. It is still another object to provide novel compositions of matter suitable for use in the aforesaid methods. Other objects will be apparent to those skilled in the art to which this invention pertains.

SUMMARY OF THE INVENTION

In a process aspect, this invention relates to a method for reducing the toxic effects of acetaminophen ingested in humans which comprises administering to a human ingesting an amount of acetaminophen capable of manifesting toxic effects therein, proximate the time of acetaminophen ingestion, a non-toxic amount effective to at least ameliorate the toxic effects of the ingested acetaminophen which would otherwise manifest themselves, of methionine sulfoxide.

In a composition aspect, this invention relates to a pharmaceutical composition comprising, in unit dosage form, an analgesic or antipyretic effective amount of acetaminophen in admixture with a non-toxic hepatotoxicity protecting amount of methionine sulfoxide. Such compositions are preferably adapted for oral ingestion and most preferably are in the form of tablets.

DETAILED DISCUSSION

In order to be both a commercially and pharmaceutically acceptable means of reducing the toxic effects in humans of ingested acetaminophen, the hepatoxicity protecting agent employed in this invention must be (a) non-toxic, i.e., it must be substantially free from any significant toxic effects at its therapeutic dosage;

(b) stable, i.e., have a shelf-life of at least six months, preferably at least one year, and more preferably at least two years in conventional pharmaceutical forms, e.g., tablets, capsules, pills, elixirs and other aqueous vehicles;

(c) non-volatile, i.e., a liquid or preferably a solid exhibiting no significant vapor pressure under ambient conditions;

(d) substantially free of subjective symptomology, i.e., which do not exhibit significant symptoms detectable to the person ingesting the sulfoxide; and (e) is in vivo hydroxyl radical-scavenging, i.e., an agent which specifically and rapidly reacts with hydroxyl radicals (HO.) generated in vivo by enzymatic or non-enzymatic processes.

Methionine sulfoxide meets all of the above criteria.

The methionine sulfoxide is preferably administered in a weight ratio to the acetaminophen of about 0.1:1 to about 10:1, more preferably about 0.2:1 to about 0.5:1. The usual oral dosage of the sulfoxide is about 1 mg/kg to about 3 mg/kg, preferably about 2 mg/kg. When administered intravenously, it is preferably administered at a rate of about 0.5 mg/min. to about 1 mg/min., preferably about 0.75 mg/min. in a total amount of about 50 mg. to about 100 mg., preferable about 75 mg.

To prevent occasional hepatoxicity associated with therapeutic dosages of acetaminophen, the methionine sulfoxide is preferably administered orally within about 8 hours, preferably within 2 hours, of the administration of the acetaminophen and most preferably concurrently therewith. When administered to prevent the hepatotoxicity associated with an overdose of acetaminophen, the methionine sulfoxide preferably is administered intravenously, e.g., as an infusion, or i.p., within 4 hours and preferably within 1 hour of the overdose.

The following is an animal study which verifies the toxicity-inhibiting activity of the methionine sulfoxide of this invention.

Hamsters weighing about 70 gm. each were divided into five groups of animals. An aqueous solution (ca. 0.7 ml) of 60 mg. (600 mg/kg) of acetaminophen and an amount of methionine sulfoxide listed in the table below, was administered intraperitoneally to each hamster. All deaths occurred within 48 hours. The survivors all were alive one week later when examined again. The results of the experiment are shown in the table below.

| Group | Acetaminophen | Methionine Sulfoxide | No. Animals | % Deaths |
|---|---|---|---|---|
| 1 | 600 mg/kg | 400 mg/kg | 8 | 0 |
| 2 | 600 mg/kg | 200 mg/kg | 17 | 0 |
| 3 | 600 mg/kg | 100 mg/kg | 17 | 23.5 |
| 4 | 600 mg/kg | 50 mg/kg | 15 | 60 |
| 5 | 600 mg/kg | 0 | 17 | 94 |

It can be seen from the above table that 100 mg/kg of methionine sulfoxide protected over 75% of the hamsters and both 200 and 400 mg/kg protected all of the hamsters from the otherwise lethal dosage of acetaminophen, indicating an $ED_{50}$ of about 65 mg/kg and an $ED_{100}$ of about 135 mg/kg.

Following the above procedure, hamsters were given i.p. either 300 mg/kg of acetaminophen or 600 mg/kg BHT. No deaths occurred in either group. In contradistinction, 100% deaths occurred within 24 hours in hamsters given i.p. a mixture of 300 mg/kg of acetaminophen and 600 mg/kg of BHT, showing profound enchancement of acetaminophen toxicity. However, no deaths occurred in hamsters to whom were administered 150 mg/kg of methionine sulfoxide concurrently with the otherwise lethal combination of 300 mg/kg of acetaminophen and 600 mg/kg of BHT.

Similarly, no deaths occurred in hamsters given i.p. either 300 mg/kg of acetaminophen or from 100-300 mg/kg BHA. In contradistinction, all hamsters given i.p. a mixture of 300 mg/kg of acetaminophen and 100 mg/kg BHA go into a coma within 15-20 minutes but most survive. Higher amounts of BHA cause higher incidence of deaths. Methionine sulfoxide protects the hamsters against the enhanced acetaminophen toxicity up to dosages of about 200 mg/kg of BHA. However, the coma produced by the combination of acetaminophen and BHA was manifested even in the survivors.

Contemplated equivalents of the methionine sulfoxide employed in this invention are other hydroxyl radical scavengers which have the properties described hereinabove. Of particular importance is their ability to reach the liver as a hydroxyl radical scavenger because most in vitro hydroxyl radical scavengers either do not pass into the liver or are metabolized into an inactive metabolite.

For example, sulfoxides which are in vivo hydroxyl scavengers are within the class of sulfoxides of the formula

wherein R and R' are alike or different and are straight or branched chain alkyl, e.g., of up to 20, preferably up to 8, carbon atoms, e.g., methyl, ethyl, isopropyl; arylalkyl wherein aryl is, e.g., mono-, di- or tri-cyclic and is carbocyclic or heterocyclic, e.g., containing one or more of N, S, O, Si and P, preferably N and/or O, as ring carbon atoms, e.g., pyridyl, pyrimidyl, pyrazinyl, indolyl, thiophenyl, furanyl, pyrrolyl, imidazolyl and benzofuranyl; a sugar moiety, e.g., glucosyl, fructosyl, manitolyl; or R and R' can be a substituted aliphatic or aromatic moiety, e.g., so as individually to form an aminoacid moiety or collectively with the S→O group to form a sulfoxide derivative of an aminoacid. Because it is its hydroxyl radical scavenging activity rather than its exact chemical structure (other than the sulfoxide group) which is critical to this invention, it will be apparent to those skilled in the art that structurally widely diverse sulfoxides can be employed in this invention, so long as they meet the criteria listed hereinabove.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

In a conventional manner, fill gelatine capsules with or prepare compressed tablets containing 500 mg of acetaminophen and 125 mg. of methionine sulfoxide per capsule or tablet. Administer two capsules or tablets three or four times daily to an adult for relief of pain and/or fever, thereby protecting the adult from hepatotoxicity which otherwise would be manifested by the adult.

Similarly, tablets and capsules containing 325 mg/75 mg. or 650 mg/150 mg. of acetaminophen/methionine sulfoxide administered at the same rate produce a far lower incidence of hepatotoxic effects, compared to the corresponding amounts of acetaminophen when administered alone.

EXAMPLE 2

Prepare an alcoholic (8½%) mint-flavored and sweetened solution of 1,000 mg. of acetaminophen and 250 mg. of methionine sulfoxide per fluid oz. (30 ml.). Administer ⅔ fl. oz. up to 6 times daily or to 1 fl. oz. up to 4 times daily, every 4-6 hours, for the relief of pain and/or fever.

EXAMPLE 3

In a conventional manner, prepare sugar coated scored chewable fruit flavored tablets each containing 80 mg. acetaminophen and 20 mg of methionine sulfoxide. Administer to children for pain and/or fever, at a dosage of 1½ tablets for children up to 3 years; 2½ tablets for children of 4-5 years; 3 tablets for children 6-8 yrs.; and 4 tablets for children 9-12 years, up to 3 or 4 times daily.

EXAMPLE 4

As part of the treatment of a massive overdosage of acetaminophen, administer to the patient intravenously 1,250 mg of methionine sulfoxide at a rate of 85 mg/min. as a 1.25% solution in isotonic salt solution.

EXAMPLES 5-11

The following are further illustrations of acetaminophen compositions of this invention which have a lower incidence of hepatotoxic side effects than the corresponding compositions which lack the acetaminophen.

| Form | Acetaminophen (mg) | Methionine Sulfoxide (mg) | Other Active Ingredients | Dosage | X per day |
|---|---|---|---|---|---|
| Suppository (ped.) | 120 | 30 | — | 1-2 | up to 6 |
| Suppository | 60 | 15 | | | |
| Tablet | 250 | 65 | Salicylamide (250 mg.) | 1-2 | 4 |
| | 300 | 70 | Salicylamide (200 mg.) | | |
| | | | Codiene phos. (32 mg.) | 1-2 | up to 6 |
| Capsules | 325 | 85 | Phenylephrine HCl (5 mg.) | | |
| | | | Codiene phos (8 mg.) Chlorpheniramine maleate (1 mg.) | 1-2 | up to 6 |
| Tablets (scored) | 300 | 70 | Allobarbital (15 mg.) | 1-2 | up to 4 |
| Tablets | 325 | 85 | Phenylpropanolamine HCl (18 Mg.) | 1-2 | up to 4 |
| Tablets | 300 | 70 | Chlorzoxazone (250 mg) | 2 | up to 4 |
| Elixir | 120/5 ml. | 30/5ml. | — | 15 ml. | up to 4 |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of reducing the chronic or acute toxic effects of acetaminophen in humans which comprises administering to a human ingesting a toxic amount of acetaminophen, a nontoxic ameliorative amount of methionine sulfoxide, said administration of methionine sulfoxide being proximate in time to said ingestion of acetaminophen.

2. A method according to claim 1 wherein the methionine sulfoxide is administered concomitantly with the acetominophen.

3. A method according to claim 1 wherein the methionine sulfoxide is administered orally.

4. A method according to claim 1 wherein the amount of acetaminophen ingested is within the analgesic effective therapeutic range and the methionine sulfoxide is administered orally simultaneously therewith.

5. A method according to claim 1 wherein the amount of acetaminophen ingested is in the overdose range and the methionine sulfoxide is administered within 4 hours after the ingestion thereof.

6. A method according to claim 5 wherein the methionine sulfoxide is administered parenterally.

7. A method according to claim 2 wherein the methionine sulfoxide is administered in physical admixture with the acetaminophen.

8. A pharmaceutical composition comprising, in unit dosage form, an analgesic or antipyretic effective amount of acetaminophen in admixture with a non-toxic amount of methionine sulfoxide which is effective to reduce the incidence of side effects associated with acetaminophen therapy.

9. A pharmaceutical composition according to claim 8, adapted for oral ingestion.

10. A pharmaceutical composition according to claim 8, in the form of a tablet.

* * * * *